US012422308B2

(12) United States Patent
Taguchi et al.

(10) Patent No.: US 12,422,308 B2
(45) Date of Patent: Sep. 23, 2025

(54) DEEP TEMPERATURE MEASURING DEVICE AND DEEP TEMPERATURE MEASURING METHOD

(71) Applicant: SEMITEC Corporation, Tokyo (JP)

(72) Inventors: Katsuhisa Taguchi, Tokyo (JP); Toshiyuki Nojiri, Tokyo (JP)

(73) Assignee: SEMITEC Corporation, Tokyo (JP)

( * ) Notice: Subject to any disclaimer, the term of this patent is extended or adjusted under 35 U.S.C. 154(b) by 0 days.

(21) Appl. No.: 18/869,903

(22) PCT Filed: May 9, 2023

(86) PCT No.: PCT/JP2023/017449
§ 371 (c)(1),
(2) Date: Nov. 27, 2024

(87) PCT Pub. No.: WO2023/228726
PCT Pub. Date: Nov. 30, 2023

(65) Prior Publication Data
US 2025/0172439 A1    May 29, 2025

(30) Foreign Application Priority Data
May 27, 2022   (JP) .................................. 2022-087131

(51) Int. Cl.
*G01K 7/22*      (2006.01)
*A61B 5/00*      (2006.01)
(Continued)

(52) U.S. Cl.
CPC .............. *G01K 7/22* (2013.01); *A61B 5/0008* (2013.01); *G01K 13/20* (2021.01); *A61B 5/01* (2013.01); *A61B 2562/0271* (2013.01)

(58) Field of Classification Search
CPC ........ G01K 7/22; G01K 13/20; A61B 5/0008; A61B 5/01; A61B 2562/0271
See application file for complete search history.

(56) References Cited

U.S. PATENT DOCUMENTS 8,716,629 B2 *   5/2014   Klewer .................. G01K 13/20
                                                                219/211
9,113,774 B2 *   8/2015   Goto ...................... G01K 13/20
(Continued)

FOREIGN PATENT DOCUMENTS

CN       111513686 A      8/2020
CN       111964800 A     11/2020
(Continued)

OTHER PUBLICATIONS

Corresponding Chinese patent application (No. 202380043040.1) issued on May 29, 2025 and English translation thereof.

*Primary Examiner* — Laura Martin
*Assistant Examiner* — Philip L Cotey
(74) *Attorney, Agent, or Firm* — Muncy, Geissler, Olds & Lowe, P.C.

(57) ABSTRACT

Provided is a deep temperature measuring device and a deep temperature measuring method capable of measuring a deep temperature of a measured object with high precision, high accuracy, and high-speed responsiveness. The above-described problem is solved by a deep temperature measuring device comprising a thermosensitive part (Ts) that senses temperature, a measurement thin film thermistor capable of measuring temperature by the thermosensitive part (Ts) being brought into contact with a measured object, a heating element layer that heats the measurement thin film thermistor, a control thin film thermistor disposed sandwiching a first heat-insulating layer with the measurement thin film thermistor and the control thin film thermistor and configured to control a temperature of the heating element layer so that the temperature is equal to a temperature of the measurement thin film thermistor, and a second heat-insulating layer that covers the heating element layer.

9 Claims, 8 Drawing Sheets

(51) Int. Cl.
 *A61B 5/01* (2006.01)
 *G01K 13/20* (2021.01)

(56) References Cited

U.S. PATENT DOCUMENTS

| | | | |
|---|---|---|---|
| 10,175,120 B2 * | 1/2019 | Nakagawa | G01K 7/02 |
| 2010/0268113 A1 | 10/2010 | Bieberich | |
| 2011/0158284 A1 * | 6/2011 | Goto | G01K 7/427 |
| | | | 374/E13.002 |
| 2011/0249699 A1 * | 10/2011 | Bieberich | G01K 13/20 |
| | | | 374/1 |
| 2012/0238901 A1 * | 9/2012 | Augustine | A61B 5/01 |
| | | | 600/549 |
| 2015/0313474 A1 * | 11/2015 | Goto | A61B 5/6833 |
| | | | 600/549 |
| 2020/0037884 A1 * | 2/2020 | Ishida | A61B 5/01 |
| 2020/0359906 A1 * | 11/2020 | Tanaka | A61B 5/6802 |
| 2021/0038084 A1 * | 2/2021 | Dion | G01K 13/20 |
| 2022/0128413 A1 * | 4/2022 | Smits | G01K 1/165 |

FOREIGN PATENT DOCUMENTS

| | | |
|---|---|---|
| JP | S54-19899 Y | 7/1979 |
| JP | 2013-524236 A | 6/2013 |
| JP | 5779806 B2 | 9/2015 |
| JP | 2016-114467 A | 6/2016 |
| JP | 6038890 B2 | 12/2016 |
| JP | 2020-016484 A | 1/2020 |
| JP | 2022-3309 A | 1/2022 |

\* cited by examiner

This embodiment

Comparative example

DEEP TEMPERATURE MEASURING DEVICE AND DEEP TEMPERATURE MEASURING METHOD

FIELD OF THE INVENTION

The present invention relates to a deep temperature measuring device and a deep temperature measuring method suitable for measuring a deep temperature of a living body as a measured object.

BACKGROUND ART

Deep temperature measuring devices that measure a temperature of a deep part of a measured object are known. For example, in a case in which the measured object is a living body of a human or an animal, a body temperature of the living body can be distinguished between a core part and a body surface part. The core part is tissue inside the living body, and a temperature thereof is not affected by heat dissipation to a surrounding environment. In contrast, the body surface part is affected by heat exchange with the surrounding environment, and a temperature thereof readily fluctuates.

In a case in which the body temperature of a living body is measured as the measured object, it is important to measure and identify the temperature of the core part to confirm a disease or a condition of the measured person (living body). Thus, deep thermometers that non-invasively measure the temperature of the core part have been developed, taking into consideration the safety of and a reduction in burden on the measured person.

In the related art, for example, a deep temperature measuring device has been proposed in which a control thermosensitive element and a measurement thermosensitive element of a heating element are provided with a heat-insulating layer interposed therebetween, and the deep temperature is measured by applying a state in which temperatures of the measurement thermosensitive element and the control thermosensitive element are in equilibrium, a so-called zero heat flux state.

PRIOR ART DOCUMENTS

Patent Documents

Patent Document 1: Japanese Patent No. 5779806
Patent Document 2: Japanese Patent No. 6038890
Patent Document 3: Japanese Unexamined Utility Model Application Publication No. S54-19899

SUMMARY OF THE INVENTION

Problems to be Solved by the Invention

However, the thermosensitive element in the deep temperature measuring device in the related art is specifically a chip-type bulk-structured negative temperature coefficient (NTC) thermistor and has a large heat capacity and limited temperature responsiveness, making it difficult to expect high-speed responsiveness.

An object of an embodiment of the present invention is to provide a deep temperature measuring device and a deep temperature measuring method capable of measuring a deep temperature of a measured object with high precision, high accuracy, and high-speed responsiveness.

Means for Solving the Problems

A deep temperature measuring device according to an embodiment of the present invention comprises a thermosensitive part that senses temperature, a measurement thin film thermistor capable of measuring temperature by the thermosensitive part being brought into contact with a measured object, a heating element layer that heats the measurement thin film thermistor, a control thin film thermistor disposed sandwiching a first heat-insulating layer with the measurement thin film thermistor and configured to control a temperature of the heating element layer so that the temperature is equal to a temperature of the measurement thin film thermistor, and a second heat-insulating layer that covers the heating element layer.

The deep temperature measuring device of such an embodiment is used, making it possible to measure the deep temperature of the measured object with high precision, high accuracy, and high-speed responsiveness.

A deep temperature measuring method according to an embodiment of the present invention includes a thermosensitive part that senses temperature, a measurement thin film thermistor capable of measuring temperature by the thermosensitive part being brought into contact with a measured object, a heating element layer that heats the measurement thin film thermistor, a control thin film thermistor disposed sandwiching a first heat-insulating layer with the measurement thin film thermistor and configured to control a temperature of the heating element layer so that the temperature is equal to a temperature of the measurement thin film thermistor, and a second heat-insulating layer that covers the heating element layer. The deep temperature measuring method comprises bringing the thermosensitive part into contact with the measured object, detecting, by the control thin film thermistor, heat radiated from the measurement thin film thermistor, controlling a heating temperature of the heating element layer in accordance with a temperature difference between a detected temperature of the measurement thin film thermistor and a detected temperature of the control thin film thermistor, detecting a thermal equilibrium state in which the temperatures of the measurement thin film thermistor and the control thin film thermistor are equal, and outputting a measurement result of a deep temperature of the measured object.

Effect of the Invention

According to an embodiment of the present invention, it is possible to provide a deep temperature measuring device and a deep temperature measuring method capable of measuring a deep temperature of a measured object with high precision, high accuracy, and high-speed responsiveness.

EMBODIMENTS OF THE INVENTION

Figure 1:
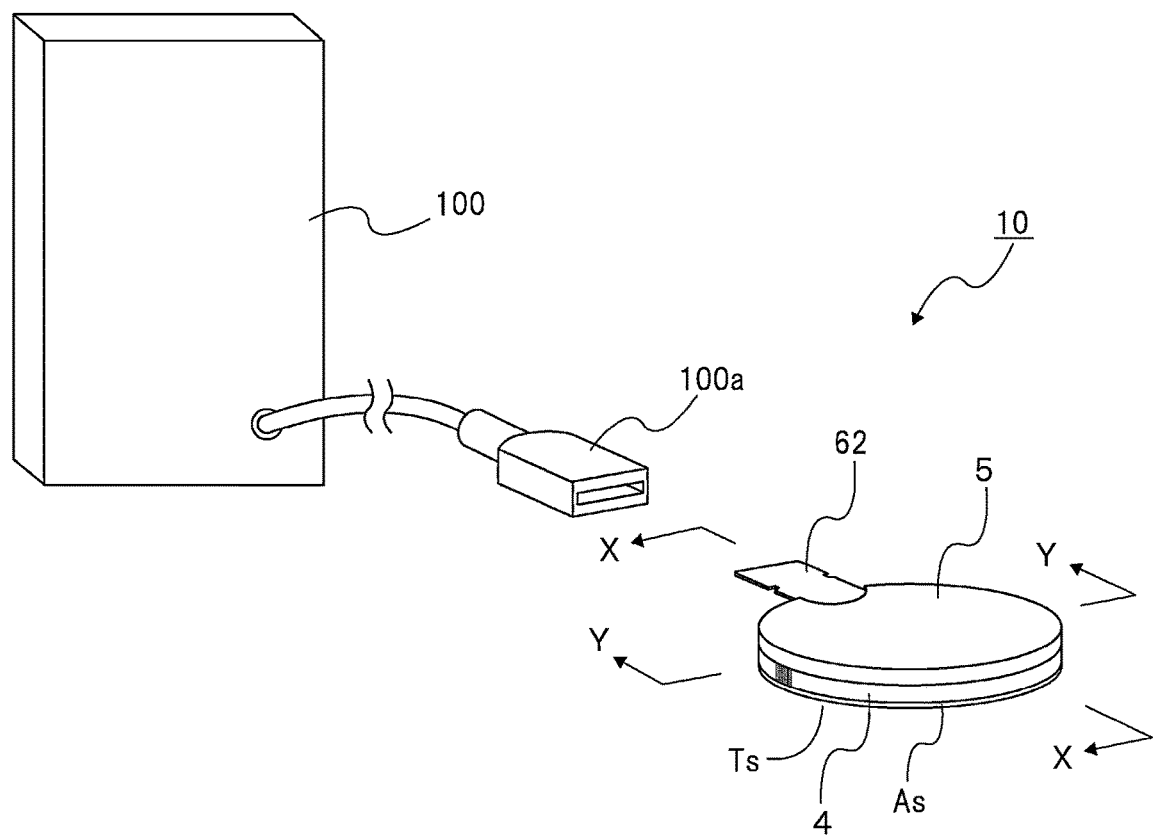
FIG. 1 is a perspective view illustrating a deep temperature measuring device according to an embodiment of the present invention.
Figure 2:
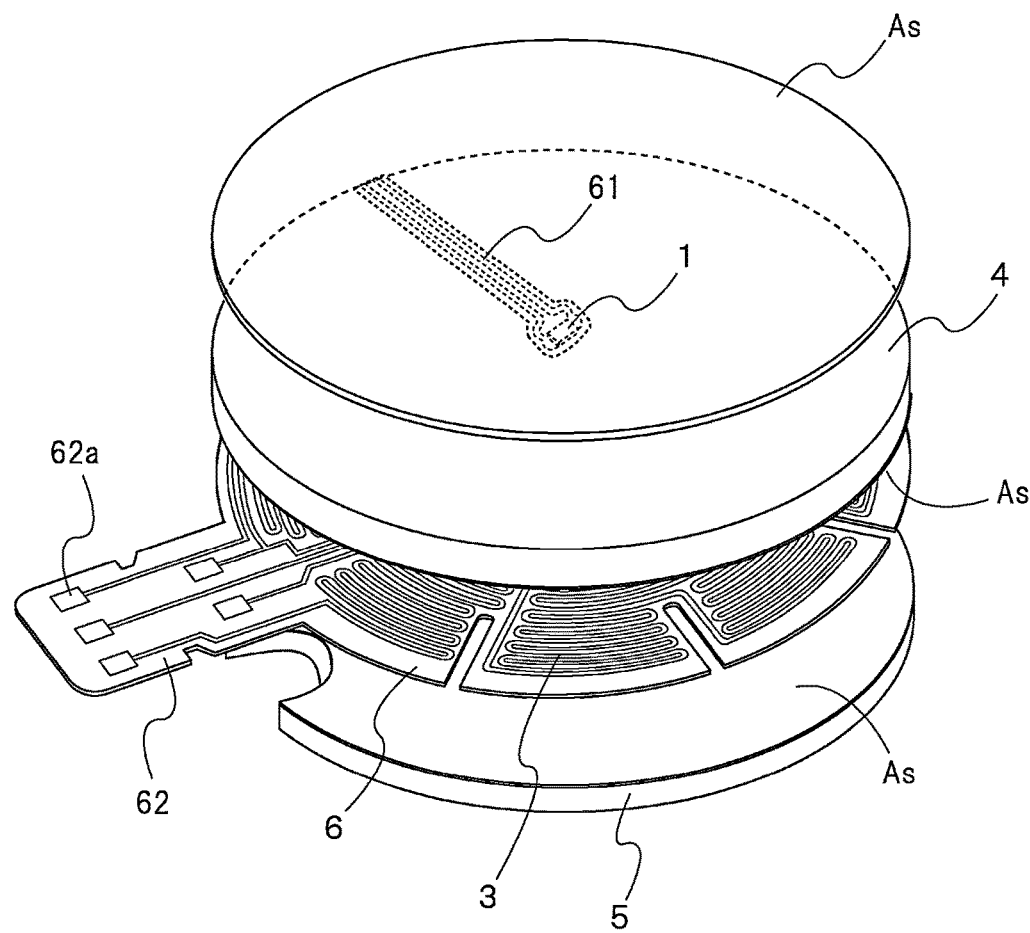
FIG. 2 is an exploded perspective view of the same deep temperature measuring device as viewed from a measurement thermosensitive element side.
Figure 3:
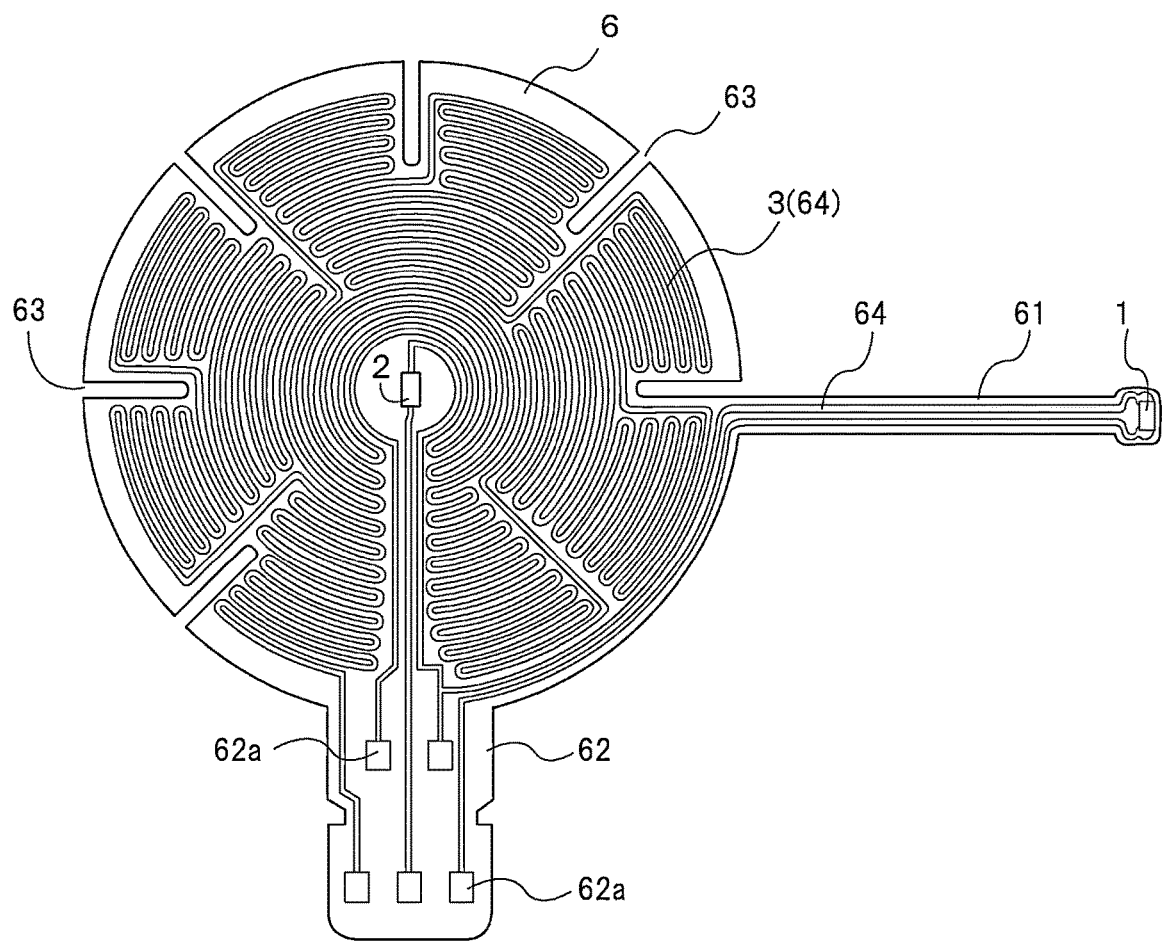
FIG. 3 is a plan view illustrating the measurement thermosensitive element, a heating element layer, and a control thermosensitive element of the heating element layer, mounted on a circuit board of the same deep temperature measuring device.
Figure 4:
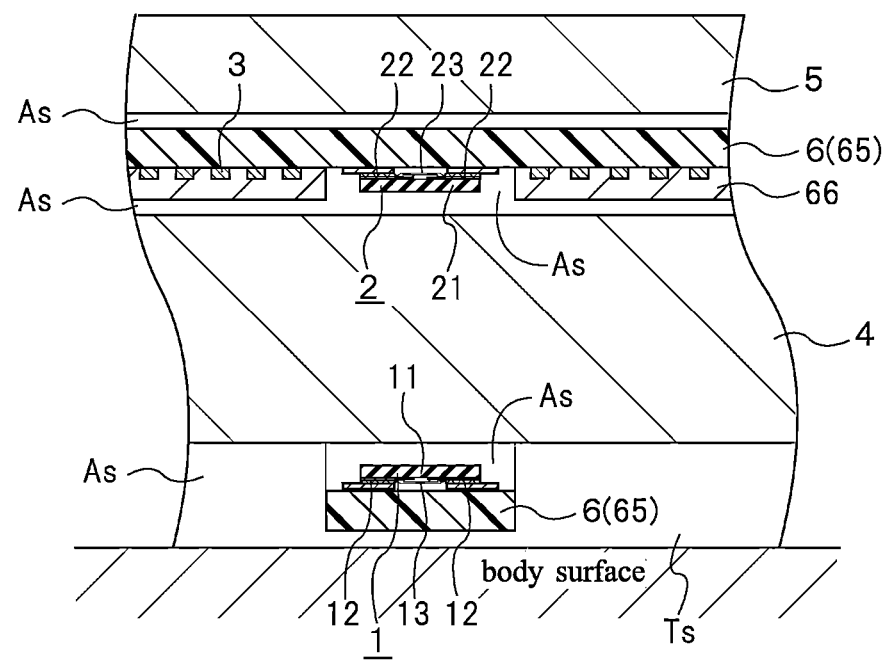
FIG. 4 is a sectional view illustrating a schematic portion along line X-X in FIG. 1.
Figure 5:
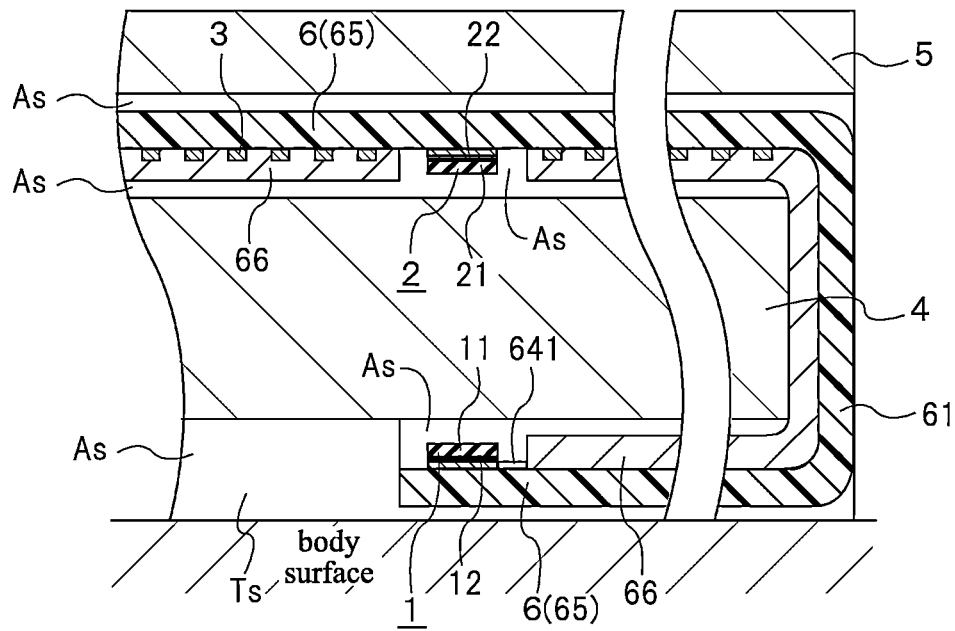
FIG. 5 is a sectional view illustrating a schematic portion along line Y-Y in FIG. 1.
Figure 6:
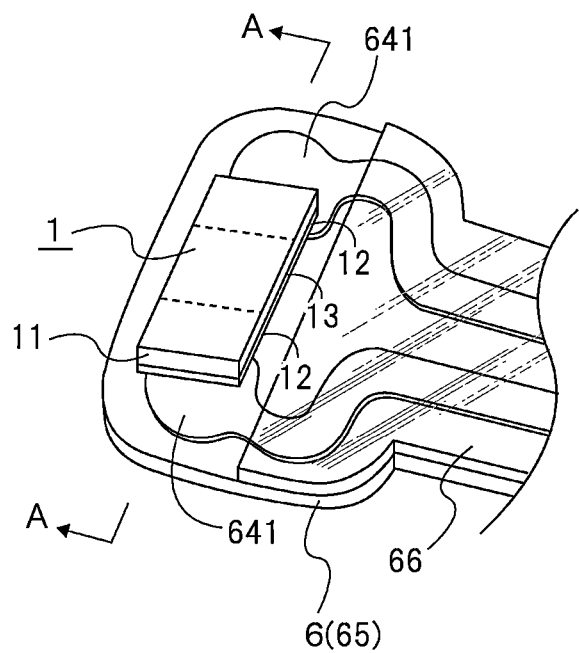
FIG. 6 is an enlarged perspective view illustrating the measurement thermosensitive element in the same deep temperature measuring device.
Figure 7:
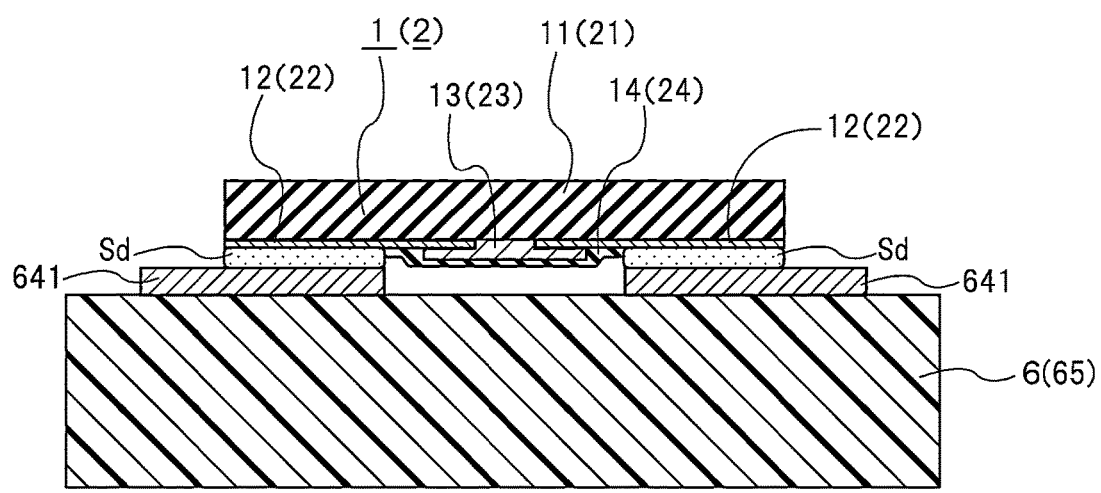
FIG. 7 is a sectional view illustrating the measurement thermosensitive element cut along line A-A in FIG. 6.
Figure 8:
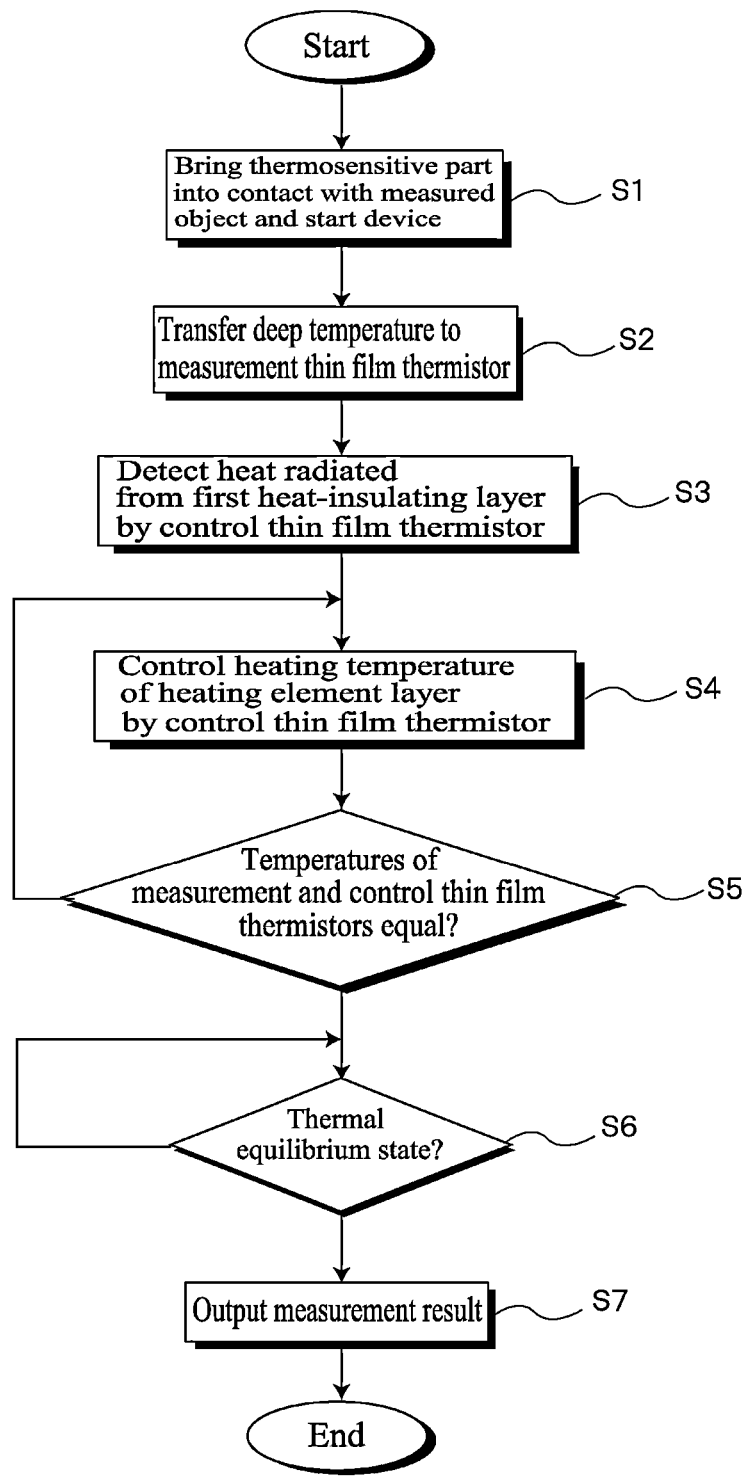
FIG. 8 is a flowchart illustrating operations of the same deep temperature measuring device.
Figure 9A:
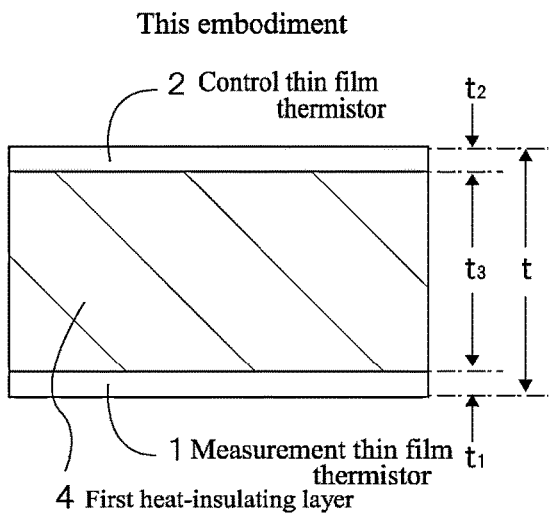
FIGS. 9(a) and 9(b) are explanatory views illustrating a relationship between thickness dimensions of this embodiment and a comparative example in the same deep temperature measuring device.
Figure 9B:
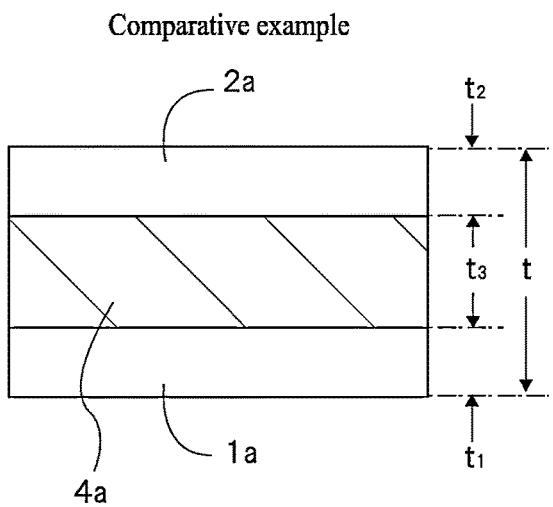
Figure 10:
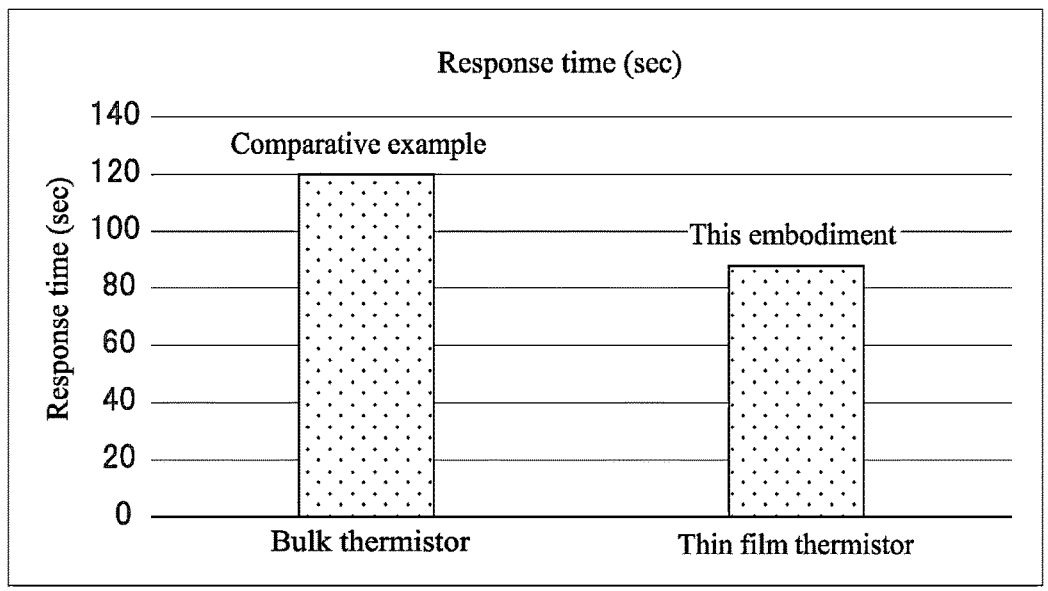
FIG. 10 is a graph showing a response time of the same deep temperature measuring device.

Hereinafter, a deep temperature measuring device and a deep temperature measuring method according to an embodiment of the present invention will be described with reference to FIG. 1 to FIG. 10. FIG. 1 and FIG. 2 are a perspective view and an exploded perspective view, as viewed from a measurement thermosensitive element side, of the deep temperature measuring device, FIG. 3 is a plan view illustrating the measurement thermosensitive element, a heating element layer, and a control thermosensitive element of the heating element layer, mounted on a circuit board, FIG. 4 is a schematic partial sectional view along line X-X in FIG. 1, and FIG. 5 is a schematic partial sectional view along line Y-Y in FIG. 1. FIG. 6 is an enlarged perspective view illustrating the measurement thermosensitive element, and FIG. 7 is an enlarged sectional view illustrating the measurement thermosensitive element. FIG. 8 is a flowchart illustrating operations of the deep temperature measuring device, FIGS. 9(a) and 9(b) are explanatory views illustrating a relationship between thickness dimensions of this embodiment and a comparative example in the deep temperature measuring device, and FIG. 10 is a graph showing a response time of the deep temperature measuring device.

It should be noted that, in each drawing, a scale of each member may be changed as appropriate in order to illustrate each member in a size enabling recognition for the purpose of description. Further, the same or equivalent portions are denoted by the same reference signs, and duplicate descriptions are omitted.

In the deep temperature measuring device of this embodiment, to measure a deep temperature of a living body as a measured object, a thermosensitive part that senses temperature is attached to a body surface, making it possible to non-invasively measure the deep temperature with high precision, high accuracy, and high-speed responsiveness. Thin film thermistors are used as a measurement thermosensitive element that senses the temperature of the body surface and a control thermosensitive element that controls power of a heating element.

As illustrated in FIG. 1 to FIG. 5, a deep temperature measuring device 10 is a probe including a thermosensitive part Ts that senses temperature, and includes a measurement thin film thermistor 1 serving as the measurement thermosensitive element, a control thin film thermistor 2 serving as the control thermosensitive element of a heating element layer, a heating element layer 3, a first heat-insulating layer 4, and a second heat-insulating layer 5. The measurement thin film thermistor 1, the control thin film thermistor 2, and the heating element layer 3 are mounted on a circuit board 6. Further, a controller 100 including a control processing unit that controls each component is provided, and the probe is connected to the controller 100 via a connector 100a.

An overall appearance of the deep temperature measuring device 10 is a thin disk shape, with an approximate total thickness dimension of about 5 mm to 6 mm and a diameter size of about 40 mm to 45 mm.

As illustrated in FIG. 3, the circuit board 6 is a flexible printed circuit (FPC) having flexibility. The circuit board 6 is formed in a substantially circular shape, and an extending part 61 that is long and thin is formed extending in a radial direction from an outer circumferential end thereof. Further, a terminal part 62 is formed extending in the radial direction from the outer circumferential end at an interval of approximately 90 degrees from this extending part 61. A connection pad 62a is formed on the terminal part 62. In addition, a plurality of slits 63 are formed in the circuit board 6 from an outer periphery toward a center portion.

The circuit board 6 includes a wiring pattern 64 of a conductor including the heating element layer 3 formed on a surface of the circuit board 6. The measurement thin film thermistor 1 is mounted on a tip portion of the extending part 61, and the control thin film thermistor 2 is mounted on the middle portion of the circuit board 6. Further, the wiring pattern 64 having a narrow, spiral shape and functioning as the heating element layer 3 is formed across substantially the entire region of the circuit board 6.

As illustrated in FIG. 4 and FIG. 5, specifically, the circuit board 6 has a thickness dimension of about 0.05 mm and is constituted by, for example, an insulating base material 65 that is film-like and composed of polyimide resin, polyethylene terephthalate (PET) resin, or the like, and a cover layer 66 composed of a polyimide film or the like and serving as an insulating layer covering the wiring pattern 64 formed on a surface of this insulating base material 65. It should be noted that the terminal part 62 is an exposed portion not covered by the cover layer 66.

As illustrated in FIG. 6 and FIG. 7, the measurement thin film thermistor 1 includes a substrate 11, electrode layers 12 formed on a surface of this substrate 11 (lower side in the drawing), a thin film element layer 13, and a protective insulating layer 14.

The substrate 11 is substantially rectangular in shape and formed of an insulating zirconia material. It should be noted that, as the material forming the substrate 11, ceramic such as aluminum nitride or a semiconductor material such as silicon or germanium may be used. An insulating thin film is formed on a surface of this substrate 11 by a sputtering method. Specifically, the substrate 11 having a rectangular shape is ultra-thin is formed to a thickness dimension of 0.3 mm or less, preferably 0.25 mm or less, and has a length dimension of 1.6 mm and a width dimension of 0.8 mm. Such a substrate 11 that is ultra-thin is used for a thin film thermistor, making it possible to realize a thermosensitive element having a small heat capacity, high sensitivity, and excellent thermal responsiveness. It should be noted that a length dimension and a width dimension of the measurement thin film thermistor 1 are also determined by the dimensions of the substrate 11, and are 1.6 mm and 0.8 mm, respectively.

A pair of the electrode layers 12 are formed on both end portions of the substrate 11. The electrode layers 12 are each formed by depositing a metal thin film by a sputtering method and, as a metal material thereof, a precious metal such as platinum (Pt), gold (Au), silver (Ag), or palladium (Pd), or an alloy thereof, such as an Ag—Pd alloy, for example, can be applied.

The thin film element layer 13 is a thermistor composition and is constituted by an oxide semiconductor having a negative temperature coefficient. The thin film element layer 13 is formed on the electrode layers 12 by a sputtering method or the like and is electrically connected to the electrode layers 12. It should be noted that the thin film element layer may be constituted by an oxide semiconductor having a positive temperature coefficient.

The thin film element layer 13 is constituted by, for example, two or more elements selected from transition metal elements such as manganese (Mn), nickel (Ni), cobalt (Co), and iron (Fe).

The protective insulating layer 14 is formed so as to cover the thin film element layer 13. The protective insulating layer 14 is a protective glass layer formed of borosilicate glass.

Further, a wiring pattern 641 extending from the extending part 61 of the circuit board 6 is joined by soldering Sd and electrically connected to the electrode layers 12.

As illustrated in FIG. 4 and FIG. 5, the measurement thin film thermistor 1 such as described above is mounted on the circuit board 6 with the thin film element layer 13 and the electrode layers 12 formed on the surface of the substrate 11 disposed facing the measured object side, that is, the body surface side serving as a contact surface. Accordingly, the measurement thin film thermistor 1 is mounted and disposed face-down on the circuit board 6.

The control thin film thermistor 2 has a function of controlling power supplied to the heating element layer 3, is the same element as the measurement thin film thermistor 1, and has the same specifications and characteristics. Accordingly, the same or equivalent portions as those of the measurement thin film thermistor 1 are denoted by the same or equivalent reference signs, and detailed descriptions thereof are omitted.

As illustrated in FIG. 3 to FIG. 5, the heating element layer 3 is formed in a pattern having a narrow, substantially spiral shape from the middle portion to an outer circumferential portion of the circuit board 6. The heating element layer 3 generates heat by power being supplied thereto.

As illustrated in FIG. 2, FIG. 4, and FIG. 5, the first heat-insulating layer 4 is formed of foamed polyethylene having heat-insulating properties and flexibility, and has the effect of suppressing the occurrence of gaps with the measured object even if the measured object is not flat. It should be noted that, in the illustrations in FIG. 4 and FIG. 5, the scale of each member is changed as appropriate for the purpose of description. Examples include the relationship between thickness dimensions of the circuit board 6 and the measurement thin film thermistor 1 as well as the control thin film thermistor 2. In reality, the thickness dimension of the circuit board 6 is less than the thickness dimension of the measurement thin film thermistor 1.

The first heat-insulating layer 4 has a circular shape of substantially the same size as that of the circuit board 6, specifically, a thickness dimension of 3.0 mm and a diameter of 42.0 mm. A double-sided adhesive sheet As having softness, flexibility, and viscosity is provided as an adhesive layer on both sides of this first heat-insulating layer 4, and the circuit board 6 is attached to both sides of the first heat-insulating layer 4. Specifically, the circuit board 6 is a single substrate, and the circular portion of the circuit board 6 is disposed on one surface side of the first heat-insulating layer 4, and the extending part 61 of the circuit board 6 is folded and disposed on the other surface side of the first heat-insulating layer 4.

Further, as illustrated in FIG. 4 to FIG. 7, a portion on which the measurement thin film thermistor 1 is mounted is an exposed portion not covered by the cover layer 66. Similarly, a portion on which the control thin film thermistor 2 is mounted is also an exposed portion not covered by the cover layer 66. Accordingly, the double-sided adhesive sheet As serving as an adhesive layer comes into direct contact with the measurement thin film thermistor 1 and the control thin film thermistor 2. Specifically, the double-sided adhesive sheet As surrounds the measurement thin film thermistor 1 and the control thin film thermistor 2 due to the viscosity thereof.

It should be noted that the length dimension and the width dimension of the measurement thin film thermistor 1 are 1.6 mm and 0.8 mm, respectively. Accordingly, ratios of the length dimension and the width dimension of the measurement thin film thermistor 1 to the diameter dimension of the first heat-insulating layer 4 are approximately 1:26 for the length dimension and approximately 1:53 for the width dimension. Thus, the ratios are increased, making it possible to sufficiently secure the heat-insulating properties. As a result of considering and examining configurations such as described above, it was found that setting the ratios of the length dimension and the width dimension of the measurement thin film thermistor 1 to the diameter dimension of the first heat-insulating layer 4 to 1:10 or greater, preferably 1:26 or greater, makes it possible to further expect secureness of the heat-insulating properties and is thus desirable.

Further, the second heat-insulating layer 5 formed of foamed polyethylene having similar heat-insulating properties and flexibility is attached to one surface side of the circuit board 6 via the double-sided adhesive sheet As having softness, flexibility, and viscosity as an adhesive layer. Incidentally, a thickness dimension of the second heat-insulating layer 5 is about 2 mm.

As described above, the measurement thin film thermistor 1, the control thin film thermistor 2, the circuit board 6, the heating element layer 3, the first heat-insulating layer 4, the second heat-insulating layer 5, and the double-sided adhesive sheet As are layered to configure a probe, and the thermosensitive part Ts is configured by the other surface side of the first heat-insulating layer 4, on which the measurement thin film thermistor 1 is positioned, and the measurement thin film thermistor 1. This thermosensitive part Ts serves as a contact surface that comes into contact with the measured object (body surface) and can be attached to the measured object by the double-sided adhesive sheet As. Adopting such a configuration has the effect of not causing a gap to occur between the measured object and the first heat-insulating layer 4. Specifically, the first heat-insulating layer 4, the second heat-insulating layer 5, the circuit board 6, and the adhesive sheet As serving as an adhesive layer are all flexible, and the probe as a whole has flexibility. Thus, whether the measured object has a flat surface or a curved surface, the thermosensitive part Ts can be brought into contact with the measured object by adapting to the shape thereof and adhering thereto without gaps using the double-sided adhesive sheet As.

Further, the measurement thin film thermistor 1 and the control thin film thermistor 2 are disposed spaced apart with the first heat-insulating layer 4 interposed therebetween. In this case, the components of the measurement thin film thermistor 1, such as the substrate 11 and the thin film element layer 13 of the measurement thin film thermistor 1, and the components of the control thin film thermistor 2, such as a substrate 21 and a thin film element layer 23 of the control thin film thermistor 2, are positioned line-symmetrically.

Next, a variation (tolerance) in resistance values of the measurement thin film thermistor 1 and the control thin film thermistor 2 will be described. For example, a resistance value indicated by a thermistor depends on constituent materials of the thermistor, a mixing ratio of the materials, manufacturing conditions, size, and the like. Therefore, the resistance value indicated by a thermistor is prone to variation and individual differences occur. Accordingly, it is expected that the variation in the resistance value can be corrected to reduce the variation and perform highly reliable temperature measurement.

In thermistors in the related art, a standard of setting the variation in resistance value within a range of ±5% when the resistance value is 10 kΩ at a room temperature of 25° C., for example, is established. However, when this is converted to temperature, an error of approximately ±2.5° C. occurs, which significantly reduces the reliability of deep temperature measurement.

Therefore, deep temperature measuring devices provided with a temperature sensor calibrating device have been provided as a means for reducing the variation. However, providing a temperature sensor calibrating device not only increases the number of parts, but also requires time for calibration. Further, there is a risk that the presence of the temperature sensor calibrating device may affect the temperature environment.

By the way, in a case in which the use of a deep temperature measuring device is considered in a medical setting, there is the YSI400 standard (which defines the resistance values used in the YSI400 series thermistor temperature sensing elements and is widely adopted as the standard for medical temperature probes and devices connected thereto.) This YSI400 standard specifies that the variation in resistance value at a room temperature of 25° C. and a resistance value of 2.2 kΩ is ±0.2%.

Accordingly, preferably at least the variation in resistance value at a room temperature of 25° C. and a resistance value of 10 kΩ is set within a range of less than ±0.5% conforming to the YSI400 standard, and more preferably the variation in resistance value at a room temperature of 25° C. and a resistance value of 2.2 kΩ is set within the range of ±0.2% conforming to the YSI400 standard.

As a processing means for suppressing such variation, in a case in which the variation in resistance value is to be corrected, a method is applied in which part of an electrode surface or a body of a thin film thermistor is cut and trimmed by laser irradiation or sandblasting. In this case, a removed portion for trimming is formed in the electrode layer or the thin film element layer of the thin film thermistor.

Further, in some cases, a means may be applied, such as uniformizing the thickness dimension of the substrate of the thin film thermistor, uniformizing a dicing size when cutting the thin film thermistors from the same wafer, and sorting the fabricated thin film thermistors.

By applying a processing means for suppressing the variation as described above, it is possible to provide the deep temperature measuring device 10 having high accuracy and high reliability without the need for a temperature sensor calibrating device.

Then, operations of the deep temperature measuring device 10, in a case in which the body temperature of a living body is measured as a measured object, will be described with reference to FIG. 8. FIG. 8 is a flowchart illustrating an overview of temperature measurement. These operations are mainly executed by a program of the control processing unit built into the controller 100.

First, the terminal part 62 of the probe is connected to the connector 100a extending from the controller 100. A strippable sheet (not illustrated) is attached to the thermosensitive part Ts in advance, and thus this strippable sheet is peeled off.

Next, the thermosensitive part Ts is attached to and brought into contact with the body surface of the measured object, and the power is turned on to start the deep temperature measuring device 10 (step S1). The deep temperature is transferred to the measurement thin film thermistor 1 (step S2). The heat of the measurement thin film thermistor 1 is radiated through the first heat-insulating layer 4. The control thin film thermistor 2 detects this radiated heat (step S3).

The heating temperature is controlled by the control thin film thermistor 2 so that power is supplied to the heating element layer 3 to generate heat in accordance with a temperature difference between a detected temperature of the measurement thin film thermistor 1 and a detected temperature of the control thin film thermistor 2 (step S4). In this case, the control thin film thermistor 2 and the heating element layer 3 are covered with the second heat-insulating layer 5, making it possible to suppress the dissipation of heat caused by wind and the like.

The measurement thin film thermistor 1 is heated and controlled by the heating element layer 3 so that the temperatures of the measurement thin film thermistor 1 and the control thin film thermistor 2 are equal, and is controlled to be in a thermal equilibrium state, that is, so that a heat flux of the first heat-insulating layer 4 interposed between the measurement thin film thermistor 1 and the control thin film thermistor 2 is in a so-called zero heat flux state (step S5). The body surface temperature in this thermal equilibrium state, that is, the detected temperature of the measurement thin film thermistor 1, can be estimated as the deep temperature, and thus thermal equilibrium is detected (step S6) and the measurement result of the deep temperature of the living body is output by being displayed or recorded by the controller 100 (step S7).

Next, effects of the thickness dimension of the heat-insulating layers will be described with reference to FIGS. 9(a) and 9(b). FIG. 9(a) is a conceptual view for explaining the effects of the thickness dimension of the heat-insulating layer of this embodiment, and FIG. 9(b) is a conceptual view for explaining the effects of a thickness dimension of a heat-insulating layer of a comparative example.

As illustrated in FIG. 9(a), in this embodiment, the first heat-insulating layer 4 and the control thin film thermistor 2 are layered on the measurement thin film thermistor 1. Here, a thickness dimension t in this layered state is approximately 3 mm, and thickness dimensions $t_1$, $t_2$ of the measurement thin film thermistor 1 and the control thin film thermistor 2 including the circuit board 6 are approximately 0.25 mm. Accordingly, a thickness dimension $t_3$ of the first heat-insulating layer 4 is approximately 2.5 mm.

On the other hand, in the comparative example of the related art illustrated in FIG. 9 (b), given that a thickness dimension t in the layered state is approximately 3 mm, a measurement thermistor 1a and a control thermistor 2a are chip-type bulk-structured thermistors, and respective thickness dimensions $t_1$, $t_2$ thereof are approximately 0.9 mm. Accordingly, a thickness dimension $t_3$ of a first heat-insulating layer 4a is approximately 1.2 mm.

Accordingly, according to this embodiment, it is possible to increase the thickness dimension $t_3$ of the first heat-insulating layer 4 and enhance a thermal resistance, and thus shorten the time required to reach the thermal equilibrium and accelerate a measurement time of the deep temperature.

Furthermore, a response time of the deep temperature measuring device will be described with reference to FIG. 10. FIG. 10 is a graph showing response times of this embodiment and the comparative example. In this embodiment, the measurement thin film thermistor 1 and the control thin film thermistor 2 are used. In the comparative example of the related art, the chip-type bulk-structured thermistor is used.

As shown in FIG. 10, the response times from when the deep temperature measuring device is started to when the measurement of the deep temperature is completed are 120 seconds in the comparative example and 88 seconds in this embodiment.

Thus, in this embodiment, measurements can be made with high-speed responsiveness. The reasons for this are attributed to the following: in this embodiment, the substrate 11 that is ultra-thin and has a small heat capacity is used for the thin film thermistor; due to the use of the thin film thermistor, the thickness dimension of the first heat-insulating layer 4 is increased, making it possible to achieve higher thermal resistance; and, in the measurement thin film thermistor 1, the thin film element layer 13 and the electrode layers 12 formed on the surface of the substrate 11 are disposed facing the body surface side serving as the contact surface that is the measured object, making it possible to smoothly transfer heat from the body surface to the measurement thin film thermistor 1.

In addition, further performance improvement can be achieved by forming a thin film thermistor on the circuit board 6 without using the substrate 11.

As described above, according to this embodiment, it is possible to measure the deep temperature of the measured object with high precision, high accuracy, and high-speed responsiveness. Further, by applying a processing means such as trimming that suppresses the variation of the measurement thin film thermistor 1 and the control thin film thermistor 2, it is possible to provide the deep temperature measuring device 10 having high accuracy and high reliability without requiring a temperature sensor calibrating device.

It should be noted that, the second heat-insulating layer 5 in this embodiment prevents the influence of external disturbances such as wind. However, an infrared reflecting layer is provided on a surface thereof, making it possible to further improve the effect of suppressing the dissipation of convective heat and radiant heat.

For the deep temperature measuring device and the deep temperature measuring method of the present invention mentioned above, a deep thermometer or the like is preferably applied to measurement of a living body, but application is not limited thereto. Application can be made in a case of measuring a deep temperature of an object in the industrial field as well. For example, application can be made in a case of predicting a service life of a secondary battery as well, by identifying temperature information of a positive electrode or the like inside the battery.

The present invention is not limited to the configuration of the above-described embodiments, and various modifications are possible without departing from the gist of the invention. Further, the above-described embodiments are presented as examples, and are not intended to limit the scope of the invention. These new embodiments can be implemented in various other forms, and various omissions, substitutions, and modifications can be made. These embodiments and modifications thereof are included in the scope and gist of the invention, and in the scope of the invention and its equivalents described in the claims.

DESCRIPTIONS OF REFERENCE NUMERALS

1 Measurement thin film thermistor
2 Control thin film thermistor
3 Heating element layer
4 First heat-insulating layer
5 Second heat-insulating layer
6 Circuit board
11, 21 Substrate
12, 22 Electrode layer
13, 23 Thin film element layer
14, 24 Protective insulating layer
61 Extending part
62 Terminal part
64 Wiring pattern
65 Base material
66 Cover layer
100 Controller
As Adhesive layer
Ts Thermosensitive part

What is claimed is:

1. A deep temperature measuring device comprising:
a layered structure including
a thermosensitive part that senses temperature and includes a measurement thin film thermistor capable of measuring temperature by being brought into contact with a measured object,
a control thin film thermistor disposed sandwiching a first heat-insulating layer with the measurement thin film thermistor and configured to control a temperature of a heating element layer that heats the measurement thin film thermistor so that temperatures of the heating element layer and the measurement thin film thermistor are made equal, and
a second heat-insulating layer that covers the heating element layer and the control thin film thermistor on the first heat-insulating layer,
the first heat-insulating layer and the control thin film thermistor being layered in this order on the measurement thin film thermistor,
a cover layer being provided that insulates and covers a mounting side of a circuit board on which the measurement thin film thermistor is mounted and serves as an exposed portion by not covering a mounting portion of the measurement thin film thermistor, thereby allowing the first heat-insulating layer to be layered directly on the measurement thin film thermistor without the cover layer being interposed therebetween, and
the measurement thin film thermistor and the control thin film thermistor each including a substrate, and a thin film element layer and an electrode layer formed on this substrate, the thin film element layer and the electrode layer of the measurement thin film thermistor being disposed facing a contact surface that is the measured object.

2. The deep temperature measuring device according to claim 1, wherein
the measurement thin film thermistor and the control thin film thermistor are trimmed to correct resistance values thereof.

3. The deep temperature measuring device according to claim 2, wherein
a variation in the resistance values of the measurement thin film thermistor and the control thin film thermistor is within a range of less than ±0.5%.

4. The deep temperature measuring device according to claim 1, wherein
a thickness dimension of the substrate of the measurement thin film thermistor is 0.3 mm or less.

5. The deep temperature measuring device according to claim 1, wherein
the first heat-insulating layer and the second heat-insulating layer have flexibility.

6. The deep temperature measuring device according to claim 1, wherein
ratios of a length dimension and a width dimension of the measurement thin film thermistor to a diameter dimension of the first heat-insulating layer are set to 1:10 or greater.

7. The deep temperature measuring device according to claim 1, wherein
the first heat-insulating layer and the second heat-insulating layer are each provided with an adhesive layer having softness and flexibility.

8. The deep temperature measuring device according to claim 1, wherein
the second heat-insulating layer is provided with an infrared reflecting layer on a surface thereof.

9. A deep temperature measuring method using a deep temperature measuring device provided with a layered structure including a thermosensitive part that senses temperature and includes a measurement thin film thermistor capable of measuring temperature by being brought into contact with a measured object, a control thin film thermistor disposed sandwiching a first heat-insulating layer with the measurement thin film thermistor and configured to control a temperature of a heating element layer that heats the measurement thin film thermistor so that temperatures of the heating element layer and the measurement thin film thermistor are made equal, and a second heat-insulating layer that covers the heating element layer and the control thin film thermistor on the first heat-insulating layer, the first heat-insulating layer and the control thin film thermistor being layered in this order on the measurement thin film thermistor,
a cover layer being provided that insulates and covers a mounting side of a circuit board on which the measurement thin film thermistor is mounted and serves as an exposed portion by not covering a mounting portion of the measurement thin film thermistor, thereby allowing the first heat-insulating layer to be layered directly on the measurement thin film thermistor without the cover layer being interposed therebetween, and
the measurement thin film thermistor and the control thin film thermistor each including a substrate, and a thin film element layer and an electrode layer formed on this substrate, the thin film element layer and the electrode layer of the measurement thin film thermistor being disposed facing a contact surface that is the measured object,
the deep temperature measuring method comprising:
bringing the thermosensitive part into contact with the measured object;
detecting, by the control thin film thermistor, heat radiated from the measurement thin film thermistor;
controlling a heating temperature of the heating element layer in accordance with a temperature difference between a detected temperature of the measurement thin film thermistor and a detected temperature of the control thin film thermistor;
detecting a thermal equilibrium state in which the temperatures of the measurement thin film thermistor and the control thin film thermistor are equal; and
outputting a measurement result of a deep temperature of the measured object.

\* \* \* \* \*